United States Patent
Hoffman

(12) 
(10) Patent No.: US 6,499,337 B2
(45) Date of Patent: Dec. 31, 2002

(54) MONITORING OF PARTICULATE MATTER IN WATER SUPPLY

(75) Inventor: Amos Hoffman, Ramat Gan (IL)

(73) Assignee: Hoffman & Hoffman Electronic and Electro Mechanical Engineering Ltd., Petach Tikva (IL)

(*) Notice: Subject to any disclaimer, the term of this patent is extended or adjusted under 35 U.S.C. 154(b) by 0 days.

(21) Appl. No.: 09/785,009

(22) Filed: Feb. 16, 2001

(65) Prior Publication Data

US 2001/0015096 A1 Aug. 23, 2001

(30) Foreign Application Priority Data

Feb. 17, 2000 (IL) .................................................. 134601

(51) Int. Cl.[7] ......................... G01N 15/06; G01N 15/00; B01D 35/12
(52) U.S. Cl. ..................... 73/61.72; 73/61.61; 73/61.63; 73/64.56; 73/863.61; 73/863.21; 422/82; 422/101; 210/302; 210/768
(58) Field of Search ........................... 73/61.72, 61.61, 73/61.63, 61.66, 61.62, 19.12, 64.65, 863.02, 863.22, 863.23, 863.21, 863.61; 422/93, 82, 101; 210/302, 768

(56) References Cited

U.S. PATENT DOCUMENTS

| | | | | |
|---|---|---|---|---|
| 2,734,378 A | * | 2/1956 | Meyers | 73/63 |
| 3,334,516 A | * | 8/1967 | Cedrone | 73/61 |
| 3,400,575 A | * | 9/1968 | Madden | 73/61 |
| 3,929,003 A | * | 12/1975 | Llewellyn | 73/61 R |
| 4,369,655 A | | 1/1983 | Scearce | 73/153 |
| 4,467,637 A | * | 8/1984 | Rumberger | 73/61 R |
| 4,583,396 A | * | 4/1986 | Hunt et al. | 73/61 R |
| 4,615,413 A | * | 10/1986 | Stevenson | 184/6.4 |
| 4,626,237 A | | 12/1986 | Galloway, Jr. | 494/37 |
| 5,095,740 A | * | 3/1992 | Hodgson et al. | 73/61 R |
| 5,134,879 A | * | 8/1992 | Wong et al. | 73/61.72 |
| 5,211,842 A | * | 5/1993 | Juss et al. | 210/87 |
| 5,250,807 A | | 10/1993 | Sontvedt | 250/303 |
| 5,403,497 A | * | 4/1995 | Schultz | 210/745 |
| 5,460,733 A | * | 10/1995 | Rasmussen et al. | 210/741 |
| 5,533,406 A | * | 7/1996 | Geise | 73/863.22 |
| 5,641,894 A | * | 6/1997 | Hosokawa | 73/64.56 |
| 5,932,795 A | * | 8/1999 | Koutrakis et al. | 73/28.01 |
| 6,205,842 B1 | * | 3/2001 | Patashnick et al. | 73/28.01 |
| 6,212,948 B1 | * | 4/2001 | Ekdahl et al. | 73/152.18 |
| 6,230,551 B1 | * | 5/2001 | Burniston | 73/61.73 |

* cited by examiner

Primary Examiner—Daniel S. Larkin
Assistant Examiner—David J. Wiggins
(74) Attorney, Agent, or Firm—Rader, Fishman & Grauder, PLLC

(57) ABSTRACT

An in-line monitoring apparatus for monitoring particulate matter in a liquid stream includes an inlet and outlet for ingress and discharge of a liquid stream. An in-line particulate matter-sampling unit is arranged for accumulation of particulate matter suspending in the liquid flow between the inlet and outlet, including an apparatus for measuring particulate matter accumulation therein. Further, there is apparatus for separating particulate matter from the liquid stream and for providing the particulate matter to the in-line sampling unit and control apparatus for operating the in-line monitoring apparatus in a first and second operative mode. In the first mode, the in-line sampling unit is operative to permit entry and accumulation of particulate matter therein for measurement by the in-line monitoring apparatus, and in the second mode, a flow of liquid along the first conduit passes through the in-line sampling unit so as to remove the particulate matter accumulations therefrom so as to flush out any particulate matter as may have accumulated in the in-line sampling unit.

16 Claims, 6 Drawing Sheets

MONITORING OF PARTICULATE MATTER IN WATER SUPPLY

FIELD OF THE INVENTION

The present invention relates to the monitoring of particulate matter in a water supply.

BACKGROUND OF THE INVENTION

There are numerous objectives for monitoring of sand content in pumped well water. Among the reasons for such monitoring are to ensure the quality of the water supply, to insure the integrity of the well bore to prevent collapse of the well, and to prevent valve wear or damage to pumping installations.

Various devices are known for measuring the sand content in a liquid stream. These devices have the drawbacks of requiring on-site sampling by a technician. Emptying and calibration of such devices are also required.

SUMMARY OF THE INVENTION

The present invention seeks to overcome disadvantages of known art by providing an in-line monitoring apparatus, which is entirely automated. This in-line monitoring apparatus monitors the need for quantitative measurement and can be set to repeatedly monitor this need at predetermined intervals. The apparatus can be brought in-line, flushed, activated to perform sand content measurement, and deactivated, entirely by remote control. This ability also provides the possibility to repeat measurements, if necessary or desired.

There is thus provided, in accordance with a preferred embodiment of the present invention, an in-line monitoring apparatus for monitoring particulate matter in a liquid stream, which includes:

an inlet for permitting ingress of a liquid stream into said in-line monitoring apparatus;

an outlet for discharging a liquid stream from said in-line monitoring apparatus;

first and second liquid flow paths each arranged to conduct a liquid flow between said inlet and said outlet;

an in-line particulate matter sampling unit arranged along said first flow path for permitting therein accumulation of particulate matter suspended in a liquid flow between said inlet and outlet, and having apparatus for measuring particulate matter accumulations therein;

apparatus for separating particulate matter from a liquid stream entering said inlet, and for providing the particulate matter to said in-line sampling unit;

first and second valves for selectably permitting liquid flow along said first and second flow paths, respectively, wherein said first valve is arranged downstream of said in-line sampling unit; and control apparatus for operating said in-line monitoring apparatus in first and second operative modes, wherein, in said first mode, said first valve is closed so as to prevent a through flow of liquid along said first liquid path, and said second valve is open, and in said second mode, said first valve is open so as to permit a through flow of liquid along second liquid path, and said second valve is closed, wherein, in said first mode, said in-line sampling unit is operative to permit entry and accumulation of particulate matter therein for measurement by said in-line monitoring apparatus, and in said second mode, a flow of liquid along said first conduit passes through said in-line sampling unit so as to remove the particulate matter accumulations therefrom so as to flush out any particulate matter as may have accumulated in said in-line sampling unit.

Further in accordance with a preferred embodiment of the present invention, said in-line sampling unit includes:

at least one sampling chamber for receiving an accumulation of particulate matter; and at least one apparatus for detecting the presence of at least a predetermined volume of particulate matter in said at least one sampling chamber, said at least one apparatus being operative to provide to said control apparatus an output signal indicative of said at least predetermined volume of particulate matter accumulation, wherein said in-line monitoring apparatus also includes flow measuring apparatus for measuring the volumetric flow rate of a liquid flowing between said inlet and said outlet operative to provide an output signal to said control apparatus indicative of a rate of liquid flow, and wherein said control apparatus is further operative to evaluate the concentration of particulated matter suspended in the liquid stream per unit flow.

Additionally, in accordance with a preferred embodiment of the present invention, said control apparatus is operable to activate said in-line monitoring apparatus in said first operative mode until detection of said at least predetermined concentration of particulate matter; and wherein, in response to an output signal received from said apparatus for detecting, said control apparatus is operative to switch said in-line monitoring apparatus to said second operative mode.

Preferably, subsequent to said removal of particulate matter from said in-line sampling unit, said control apparatus is operative to switch said in-line monitoring apparatus from said second mode to said first mode.

Alternatively, subsequent to said removal of particulate matter from said in-line sampling unit, said control apparatus is selectably operable to operate said in-line monitoring apparatus in a third mode, during which said apparatus for detecting is inactive for a preselected period of time, after which said control apparatus operates said in-line monitoring apparatus reactivates said apparatus for detecting so as to operate said in-line monitoring apparatus in said first operative mode.

Additionally, in accordance with a preferred embodiment of the present invention, the concentration of particulate matter that said in-line monitoring apparatus is operative to detect is at least approximately 100 ppm.

Further in accordance with a preferred embodiment of the present invention, the concentration of particulate matter that said in-line monitoring apparatus is operative to detect is at least approximately 50 ppm.

Further in accordance with a preferred embodiment of the present invention, the concentration of particulate matter that said in-line monitoring apparatus is operative to detect is at least approximately 1 ppm.

Additionally, in accordance with a preferred embodiment of the present invention, said abovementioned valves are solenoid-type switching valves.

Further in accordance with a preferred embodiment of the present invention, said device for selectively separating a liquid stream from any suspended particulate matter as may be contained therein is a cyclone type device.

Further in accordance with a preferred embodiment of the present invention, said at least one sampling chamber includes a first lower smaller sampling chamber and a second upper larger sampling chamber.

Additionally, in accordance with a preferred embodiment of the present invention, said in-line monitoring apparatus further includes apparatus for inducing settlement of particulate matter from said upper sampling chamber to said lower sampling chamber wherein said upper sampling chamber is formed so as to permit passage of particulate matter to said lower sampling chamber.

Further in accordance with a preferred embodiment of the present invention, apparatus for inducing settlement of particulate matter includes an inclined conduit leading from said upper sampling chamber to said lower sampling chamber.

Additionally, in accordance with a preferred embodiment of the present invention, apparatus for inducing settlement of particulate matter further includes a generally upward conduit leading out from said lower sampling chamber, for allowing a flow of liquid that has entered said lower sampling chamber via said inclined conduit, to exit it.

Further in accordance with a preferred embodiment of the present invention, said apparatus for inducing settlement of particulate matter may include a vibratory unit for vibrating said sampling unit.

Further in accordance with a preferred embodiment of the present invention, said in-line monitoring apparatus includes at least one particulate matter separator arranged along said first flow path, downstream of said in-line sampling unit and upstream of said first valve, for permitting an outflow of particulate matter flushed through said first flow path during activation in said second operative mode, thereby substantially preventing outflow thereof from said outlet.

Further in accordance with a preferred embodiment of the present invention, said in-line monitoring apparatus is arranged so as to tap in to a main-flow conduit such that a stream of liquid entering said in-line monitoring apparatus from the main flow conduit is a substantially representative sample of the liquid flowing through the main flow conduit containing a correspondingly representative volume of suspended particulate matter.

There is thus also provided, in accordance with a preferred embodiment of the present invention, a method of upward flushing of an in-line monitoring apparatus for monitoring particulate matter, which includes:

directing a flow of liquid, generally downward through an inclined conduit, to a sampling chamber, thereby generating turbulence in the sampling chamber; and flushing the sampling chamber upward, by the turbulent flow, which carries particulate matter upward, through a generally upward conduit.

BRIEF DESCRIPTION OF THE DRAWINGS

The present invention will be more fully understood and appreciated from the following detailed description, taken in conjunction with the drawings, in which.

DETAILED DESCRIPTION OF A PREFERRED EMBODIMENT

Figure 1:
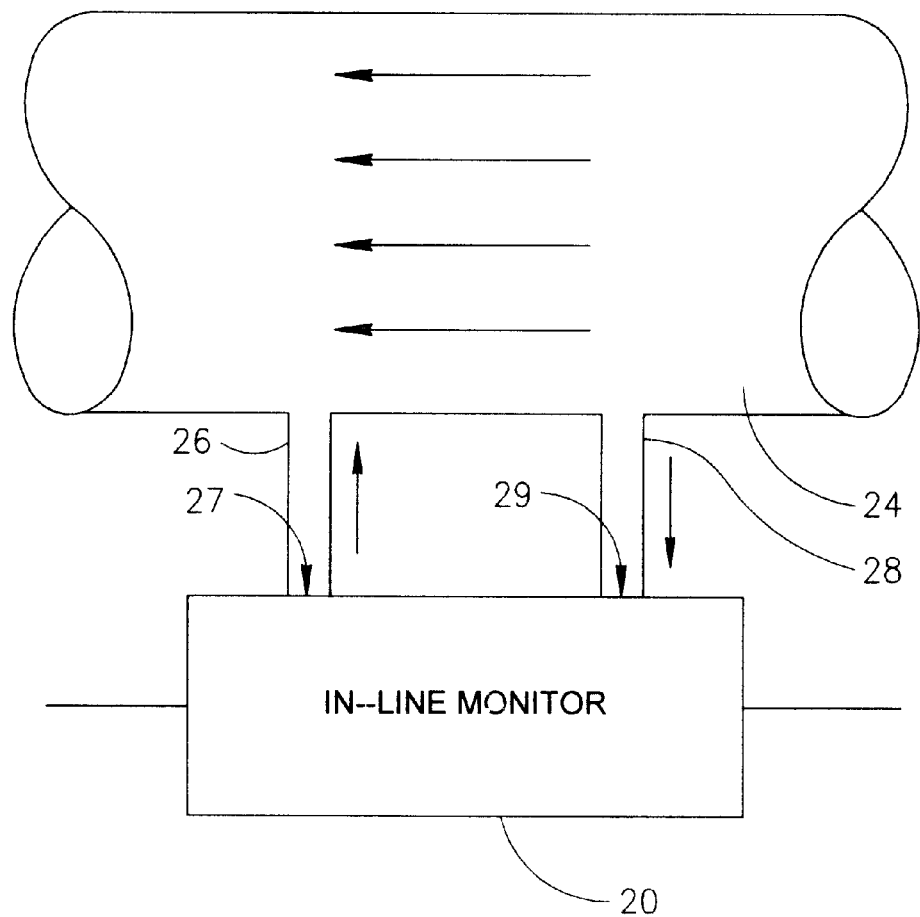
FIG. 1 is a schematic representation of a water supply conduit having connected thereto an in-line monitoring apparatus for monitoring the content of particulate matter in a stream of water.

Referring briefly to FIG. 1, there is shown an in-line monitoring apparatus, referenced generally 20, for monitoring the amount of solid particulate matter in a liquid flow. Apparatus 20 is shown in place for operation, tapping in to a main-flow conduit 24 via inlet conduit 28 and outlet conduit 26. Inlet conduit 28 is operative to convey a stream of liquid to in-line monitoring apparatus 20 via inlet 29. Preferably, outlet conduit 26 is operative to convey a stream of liquid from in-line monitoring apparatus 20 to main-flow conduit 24 via outlet 27. Alternatively, outlet conduit 26 is operative to convey a stream of liquid from in-line monitoring apparatus 20 back to a well (not shown) or to the ground, via a dry-well (not shown). Conduit 24 is typically a pipe for supplying water from a water well to a water supply network.

Figure 2:
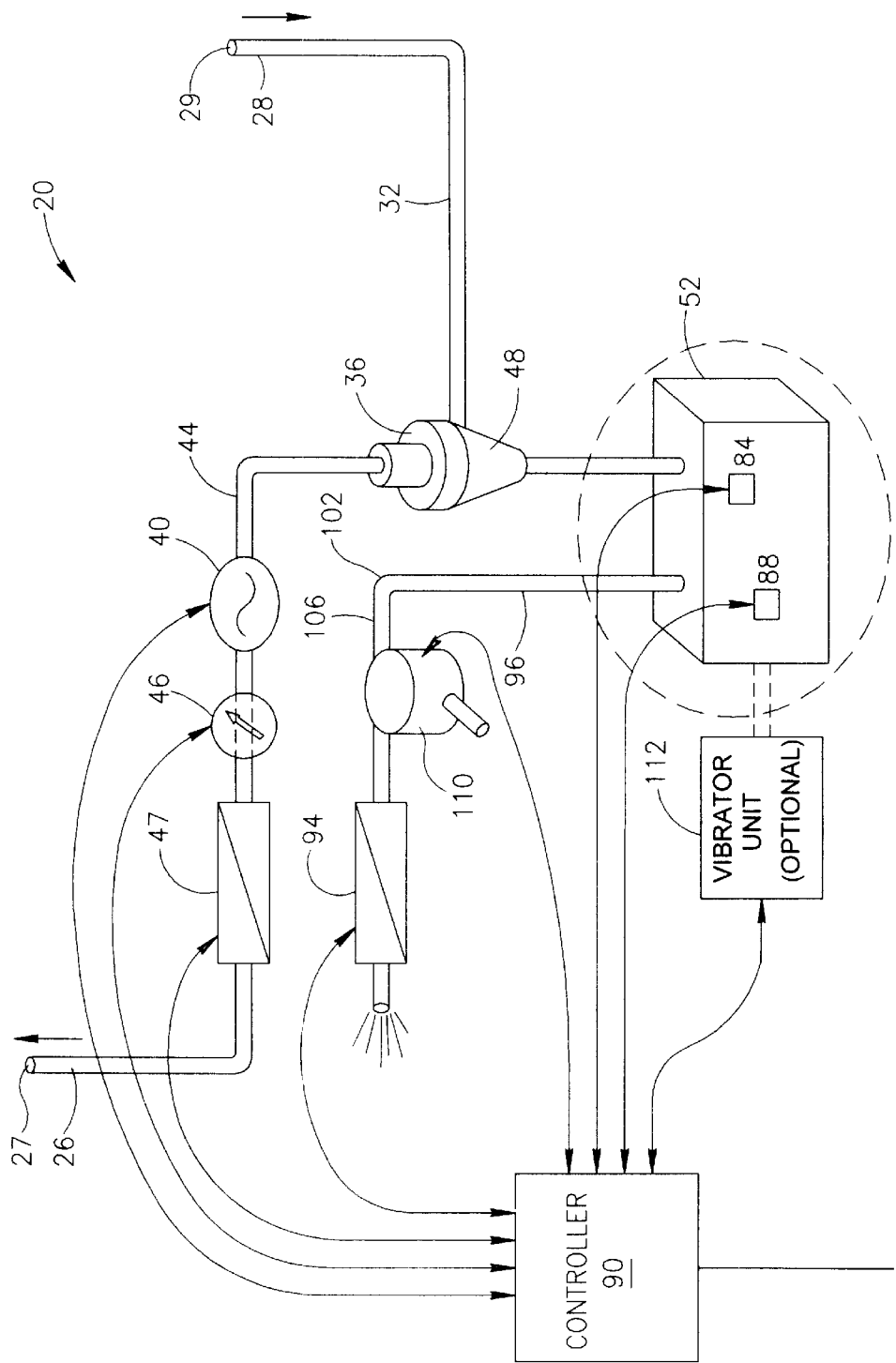
FIG. 2 shows in-line monitoring apparatus as seen in FIG. 1 which further includes controller apparatus wherein the in-line monitoring apparatus is constructed and operative in accordance with a preferred embodiment of the present invention.

Referring now to FIG. 2, the stream of liquid to be analyzed flows into in-line monitoring apparatus 20 via inlet 29, as stated above, and subsequently along conduit 32 to a cyclone 36. From Cyclone 36 the stream continues through conduit 44. Flow meter 46 is arranged along conduit 44 to measure the volumetric flow through in-line monitoring apparatus 20. Still further downstream from flow meter 46 is a valve 47, for allowing water to flow through a first flow path of the in-line monitoring apparatus 20, henceforth, a first-mode cycle, when the apparatus is monitoring the liquid stream or performing a measurement of particulate matter in the liquid stream, as described hereinbelow, and in conjunction with FIG. 5.

In a preferred embodiment of the present invention, the liquid stream through conduits 32 and 44 is forced by a pump 40 along conduit 44. Pump 40 is operative to convey the stream of liquid to outlet conduit 26, and back to main-flow conduit 24. Pump 40 is required since the pressure drop through in-line monitoring apparatus 20 is greater than that of main-flow conduit 24, running parallel to it. In an alternate embodiment of the present invention, pump 40 is not used, and from conduit 44, the stream is directed back to the well or to a dry-well.

As known in the art, cyclone 36 is operative to effectively separate any particulate matter suspended in a stream of liquid flowing through the in-line monitoring apparatus. This particulate matter settles downwards through the lower funnel-shaped portion 48 of cyclone 36 into sampling unit 52.

Figure 3:
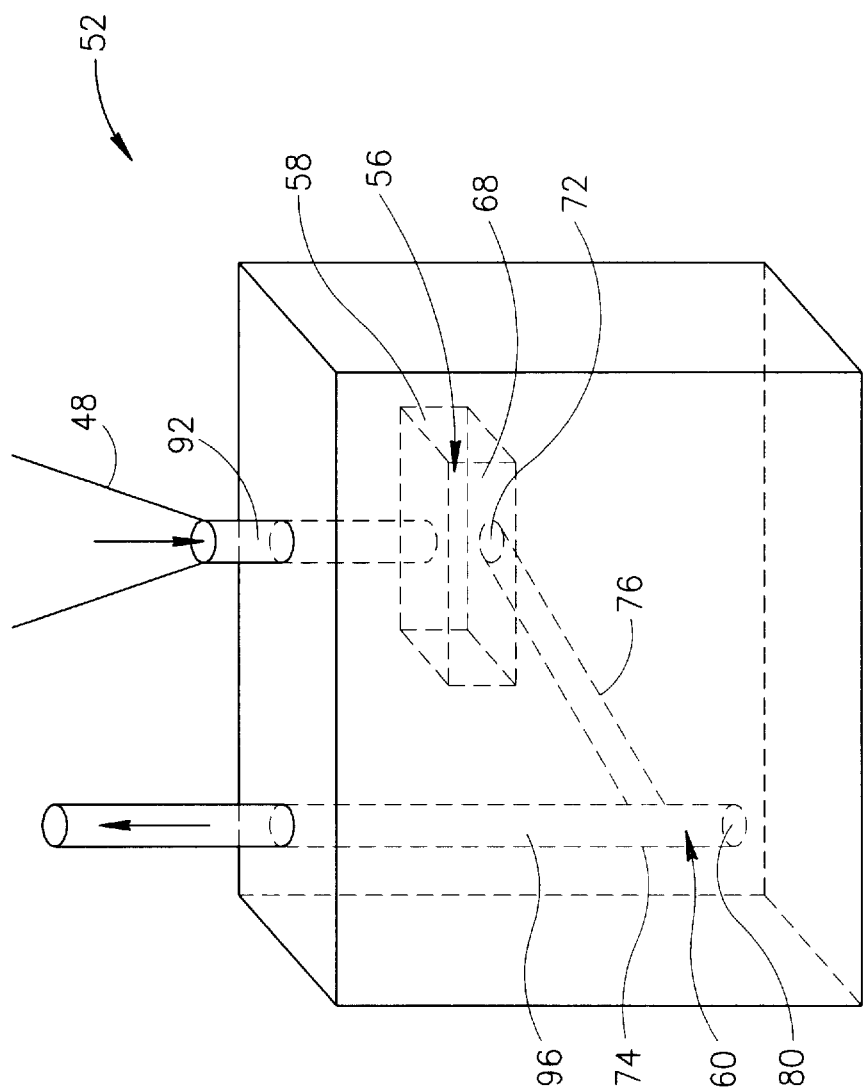
FIG. 3 is a more detailed view of the sampling unit seen in FIG. 1.

Now referring to FIG. 3, sampling unit 52 has, in a preferred embodiment of the invention, an upper sampling chamber 56, formed in an upper portion 58 of sampling unit 52; and a lower sampling chamber 60 arranged in liquid communication with and downstream of upper sampling chamber 52, connected thereto via an intermediate conduit 76. Particulate matter entering upper sampling chamber 56 begins to settle towards inclined floor element 68 of the chamber 56. Floor element 68 is sloped as a funnel, so as to facilitate settling of particulate matter towards the aperture 72 at the top of intermediate conduit 76, through intermediate conduit 76, and so on to sampling chamber 60 where it settles to the bottom surface 80 of chamber 60.

Figure 4:
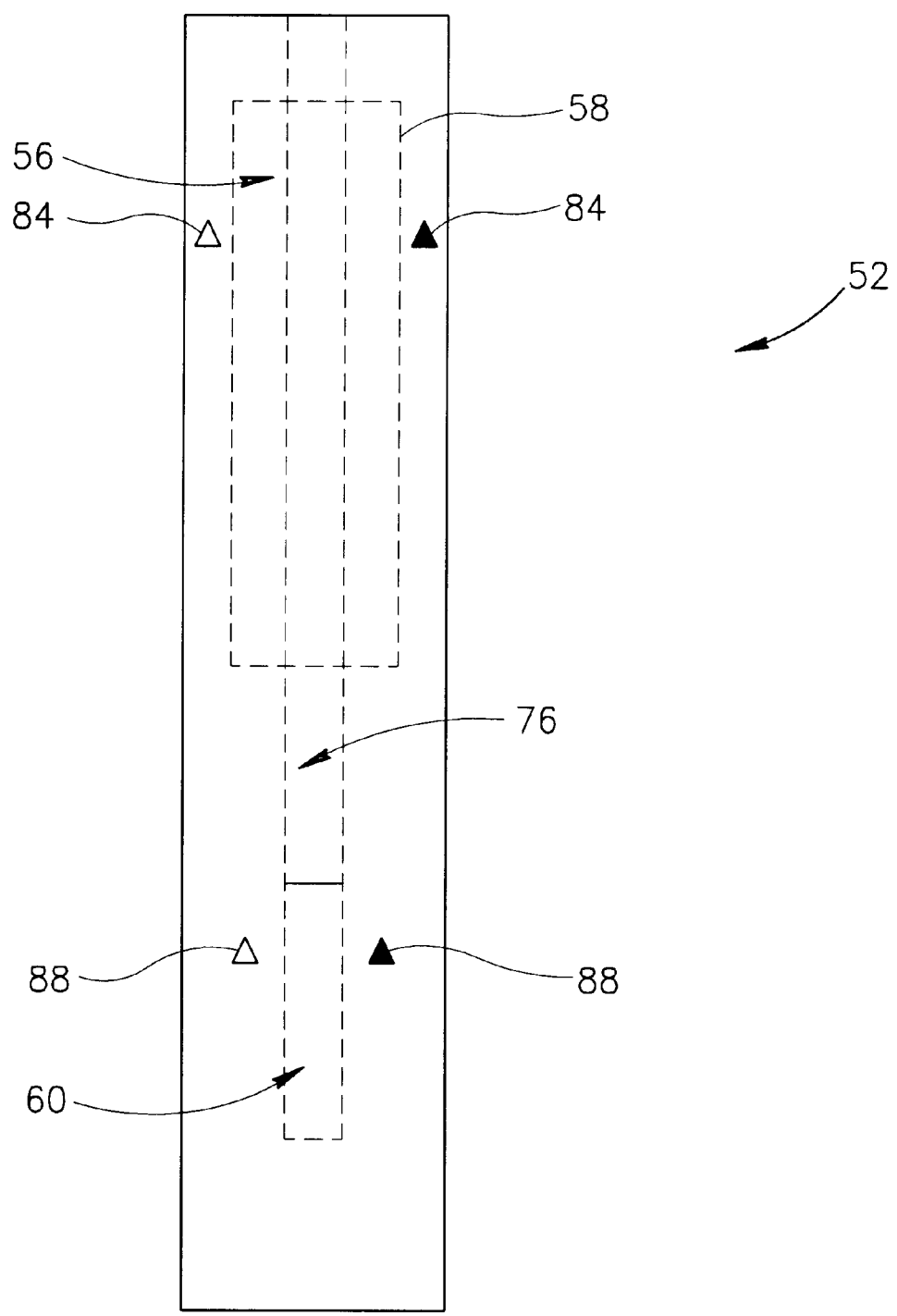
FIG. 4 is a side view of the sampling unit seen in FIG. 3 taken in the direction of arrow 4 in FIG. 3.

Referring now to FIG. 4, sampling unit 52 includes first and second optical sensor pairs 84 and 88. Optical sensor pairs 84 and 88 are operative to detect the absence or presence of particulate matter in upper sampling chamber 56 and in lower sampling chamber 60, respectively, in a manner described hereinbelow.

Referring now also to FIG. 2, sensors 84 and 88 are in electronic contact with a controller 90. Controller 90 is also in electronic contact with flow meter 46 and valve 47. Valve 47 (described above), is preferably a solenoid-type switching valve. Valve 94, described below, is a similar type valve.

A vibrator unit 112 may be provided and associated with sampling unit 52 so as to aid in the settling of any particulate matter as may enter sampling unit 52. When Vibrator unit 112 is provided, it is connected to controller 90.

Referring now again to FIG. 2, an in-line, active, measuring cycle of the herein described, in-line monitoring apparatus 20 begins when solenoid-type switching valve 47 is opened, allowing a flow of liquid through it. In consequence, a flow of liquid passes through conduits 28 and 32 before reaching cyclone 36.

When a stream of liquid reaches cyclone 36, it is diverted through a first flow path conduit 44, for example, by pump 40. Flow meter 46 measures the amount of liquid flowing through the in-line monitoring apparatus during this measuring cycle. This value will later be used to calculate the concentration of particulate matter, if any, contained in the measured volume of liquid, for example, as ppm per volume. The method of measuring and calculating is described below.

Cyclone 36 is operative to allow any particulate matter to settle downwards towards sampling unit 52.

Referring now to FIG. 3, particulate matter settles into sampling unit 52 via conduit 92 where it first enters upper sampling chamber 56.

Referring now also to FIGS. 3 and 4, as any particulate matter enters upper sampling chamber 56, sensor 84 is operative to detect the presence of amounts of particulate matter in excess of 100 ppm. The detection of this relatively larger amount of particulate matter by in-line monitoring apparatus 20 is crucial to the continued follow-through of liquid in main pipe 24. This is due to the fact that amounts of particulate matter in the range of this order of magnitude are almost always detrimental to operation of the continued follow-through of the liquid in main pipe 24. Since it is important to discover particulate matter contents of this magnitude as soon as possible, an alarm system is included with in-line monitoring apparatus 20, and is described below.

In an alternate embodiment, sensor 84 may operative to detect the presence of amounts of particulate matter in excess of 50 ppm, or another predetermined value.

Particulate matter entering upper sampling chamber 56 settles to the sloped bottom surface 68 of the chamber 56. Subsequently, particulate matter begins to settle into intermediate conduit 76. Upon reaching conduit branch 74 the particulate matter enters sampling chamber 60, where it settles to the bottom surface 80 of the chamber.

Referring now to FIG. 4, sensor element 88 is operative to detect the presence of particulate matter in sampling chamber 60 in concentrations in the order of magnitude of 1 ppm.

Flow meter 46 (FIG. 2) and sensor pairs 84 and 88 are connected to controller apparatus 90. When a line of sight between the two elements of a sensor pair, 84, for example, is obscured, a signal is sent from this sensor pair to controller 90. Since the volume of liquid that has passed through in-line monitoring apparatus 20 during a measuring cycle is measured by flow meter 46, and since the volumes of upper sampling chamber 56 and lower sampling chamber 60 are known, controller 90 can be programmed to calculate the concentration of particulate matter present in ppm.

Controller 90 can also be programmed to alert a technician if a critical situation is detected, as mentioned above. There is also the possibility to program the controller to make repeated measurements at preselected time intervals or to repeat measurements after varying time intervals depending upon the results of the previous measurement. In the preferred embodiment described herein, only two sensor pairs are employed. However, it will be appreciated by those skilled in the art, that numerous sensors may be used. Each sensor will, in such a case, correspond to a differing volume of particulate matter and a different resulting concentration of particulate matter in the monitored liquid.

A particular advantage of the present invention is the fact that it is self-flushing. The self-flushing distinguishes a monitoring cycle from a measuring cycle. Both the monitoring cycle and the measuring cycle follow the same first flow path, or the first-mode cycle, but upper sampling chamber 56 and lower sampling chamber 60 are flushed out, before and after a measurement cycle. In general, in-line monitoring apparatus 20 is in a monitoring cycle. An initiation of a measurement process, and the measurement process itself involve the following steps:

While in the monitoring cycle, any of the sensor pairs 88 or 84 (FIG. 4) report to controller 90 that the sampling chamber associated with one or both, that is any of upper sampling chamber 56 or lower sampling chamber 60, are full with particulate matter. The sampling chamber may be full either as a result of accumulation of particulate matter over a long period of time, or as a result of a problem in the liquid stream.

Controller 90 directs the liquid stream to a flushing, second flow-path, that is, a second-mode cycle, that will be described herein below, to flush out the sampling chambers;

After the flushing, controller 90 directs the liquid stream back to the monitoring-measuring flow-path;

Controller 90 takes a first reading of flow meter 46 (FIG. 2), immediately after the flushing;

Controller 90 takes a second reading of flow meter 46, when sensor pair 88 (FIG. 4) reports to controller 90 that lower sampling chamber 60 is full; and Controller 90 calculates the concentration by volume of particulate matter.

Preferably, when the calculated concentration is lower than a predetermined minimum value, for example, 1 ppm, or less, controller 90 repeats the flushing process and returns in-line monitoring apparatus 20 to a monitoring cycle. When the calculated concentration is greater than 1 ppm, the measurement process continues as follows:

Controller 90 takes a third reading of flow meter 46, when sensor pair 84 reports to controller 90 that upper sampling chamber 56 is full; and Controller 90 calculates the concentration of particulate matter.

When the calculated concentration is greater than a predetermined maximum value, for example, 50 ppm or 100 ppm, a warning signal is activated, controller 90 repeats the flushing process and returns in-line monitoring apparatus 20 to a measuring cycle.

Since each sensor can only detect sand above a particular level, additional sensors and additional chambers associated with them may be added to increase the sensitivity of in-line monitoring apparatus 20 and to insure that the initialization value for the concentration of particulate matter is below a predetermined threshold amount.

A further advantage of the present invention is that the self-flushing system is free of hidden or "blind" volumes, generally of the order of 2–4 cubic centimeters, which are associated with valves, and which introduce considerably error to the measurement. This is especially true for lower sampling chamber 60, whose volume is in the order of 0.25 cubic centimeters, much smaller than the hidden volumes associated with valves. The self-flushing system is upward-flushing, in other words, the stream of liquid and sand are flushed upward. Referring to FIGS. 2 and 3, an in-line flushing cycle, which uses the second flow-path and is designated, a second-mode cycle, begins with valve 47 closing, by controller 90, and valve 94 opening, by controller 90. The liquid stream flows from conduits 28 and 32 to cyclone 36, which is inactive as a cyclone instrument during this cycle and may be replaced, in an alternative embodiment of the invention, with a conduit. The liquid stream reaches upper sampling unit 52 via conduit 92, flushing it and carrier the particulate matter with it. The liquid stream then continues through inclined conduit 76 to lower sampling chamber 60. The turbulence produced by the liquid stream pouring out of inclined conduit 76 into lower sampling chamber 60, disturbs the particulate matter at the bottom of lower sampling chamber 60. The particulate matter is carried out, with the liquid stream, via conduit 96 to conduits 102 and 106. There is preferably a sand trap unit 110 tapping-in to conduit 106. Trap 110 works effectively as a separatory funnel type apparatus and serves to prevent large amounts of particulate matter from reaching solenoid-type switching valve 94. The liquid stream than passes through valve 94 and is poured out, to the atmosphere. (The volume of water used in the flushing cycle is relatively small, generally about 200 cc.) Alternatively, the liquid stream issuing out of valve 94 is poured back to a well, or to a dry well. In general, the flushing cycle lasts a few seconds, and after a predetermined period, controller 90 closes valve 94 and opens valve 47. In a preferred embodiment where pump 40 is used, controller 90 deactivates pump 40 with the closing of valve 47 and reactivates pump 46 with the opening of valve 47.

Figure 5:
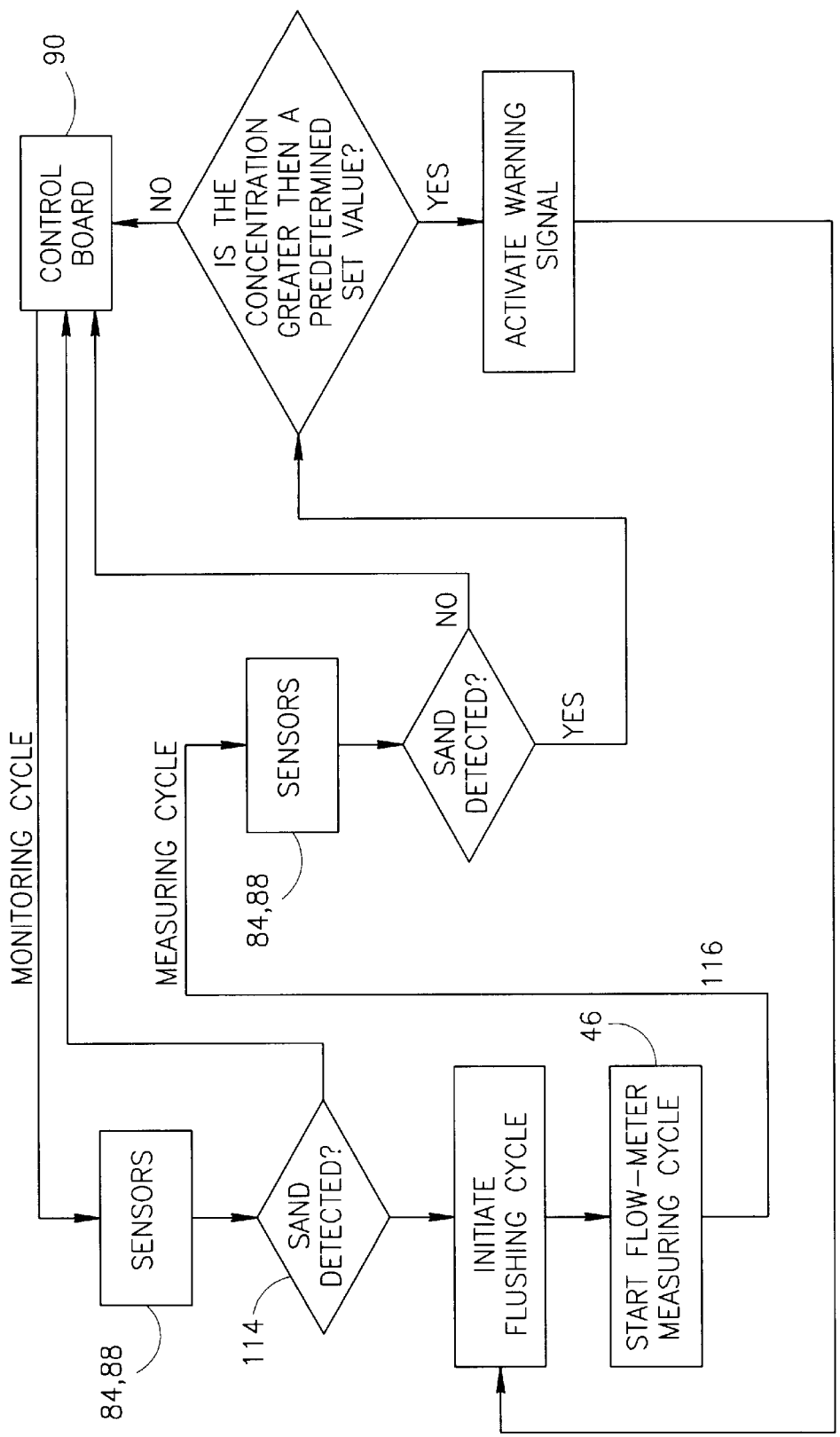
FIG. 5 is a schematic representation of a preferred embodiment of automated control in-line monitoring apparatus seen in FIG. 2.

Referring now to FIG. 5, there is seen a first preferred monitoring cycle of the in-line monitoring apparatus 20 in which controller 90 is operative to initiate testing for particulate matter in a liquid flowing through in line monitoring apparatus 20. This particular embodiment utilizes an in-line method, in which sensor pairs 84 and 88 (FIG. 4), are constantly operative to detect the presence of particulate matter. A preprogrammed detector unit 114 is operative to maintain in-line monitoring apparatus in the monitoring cycle until such time as particulate matter has indeed been detected.

When any of sensor pair 84 and 88 detects the presence of particulate matter, and detector unit 114 has been alerted to this presence, controller 90 is operative to send a signal to initiate an in-line flushing cycle as described above. When the flushing cycle is completed, a further signal is sent by controller 90 to start flow meter 46 and to begin a measuring cycle, as herein described above, and as indicated by arrow 116.

Figure 6:
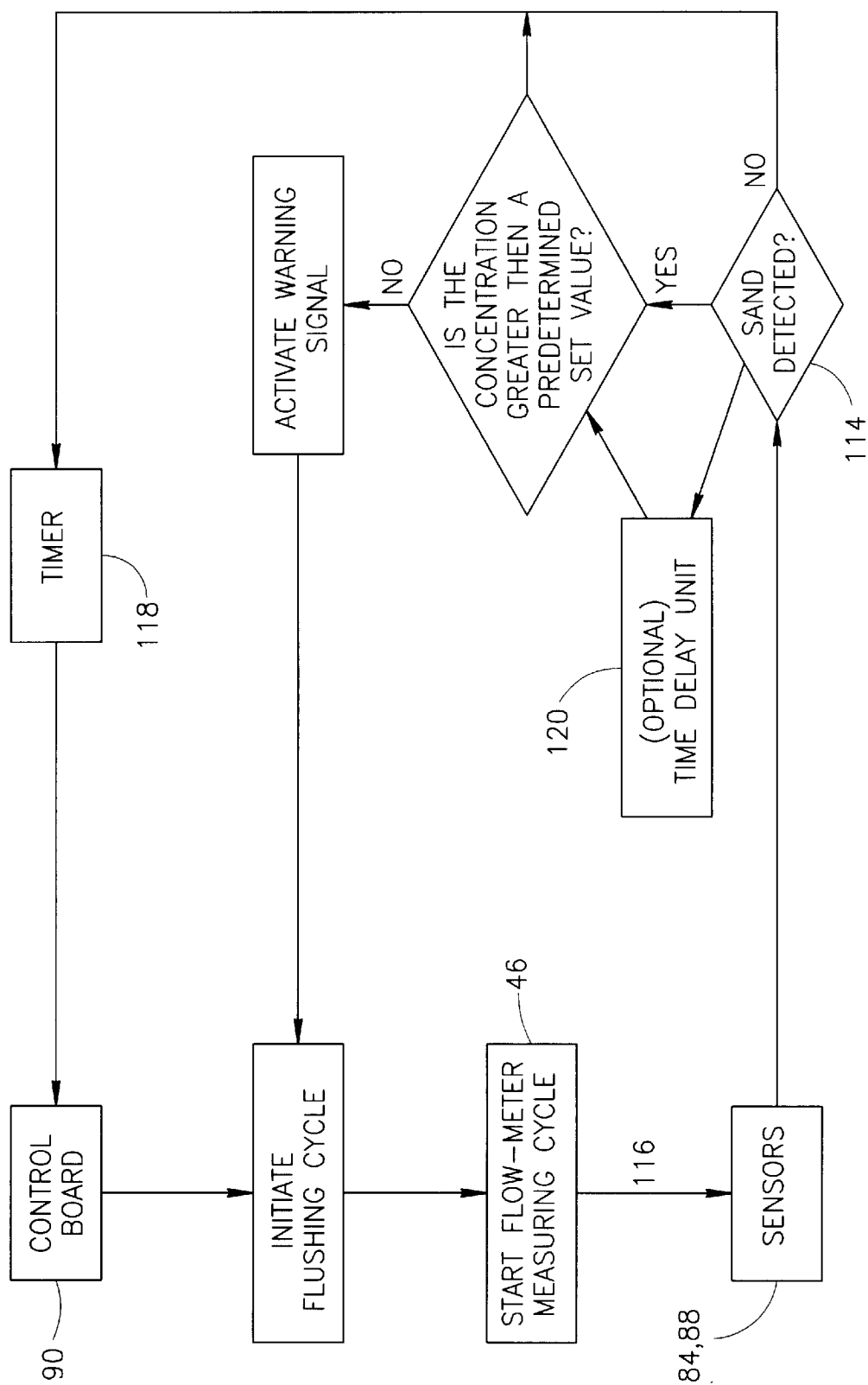
FIG. 6 is a schematic representation of an alternate embodiment of automated control in-line monitoring apparatus seen in FIG. 2.

Referring now to FIG. 6, there is seen an second preferred monitoring cycle of the present invention, in which controller 90 which is operative to initiate testing for particulate matter in a liquid flowing through in-line monitoring apparatus 20. This particular set-up utilizes a timer unit 118, which can be preprogrammed to activate in-line monitoring apparatus 20 periodically after a desired time interval has passed, such as several hours, weeks, or months.

When the predetermined time interval has expired, timer 118 sends a signal to controller 90 to initiate an in-line flushing cycle as described above. When the flushing cycle is completed, a further signal is sent by controller 90 to start flow meter 46 (FIG. 2) and to begin a measuring cycle, as herein described above, and as indicated by arrow 116.

A measuring cycle, as described above, involves activation of sensor pairs 84 and 88, in the present embodiment of the invention. After a minimum, pre-determined volume of liquid has been measured by flow meter 46, if no particulate matter is detected by sensor pairs 84 and 88, controller 90 is operative to reset timer 118 to begin timing a new time interval, until the next signal to activate the in-line monitoring apparatus is sent.

If particulate matter has been detected during this measuring cycle, the quantitative amount measured is evaluated in relation to a predetermined set value. If the amount of particulate matter measured exceeds this set value, controller 90 activates a warning or alarm to alert a human technician to take the appropriate actions indicated by this occurrence.

If the amount of particulate matter present is less than the predetermined value, controller 90 is operative to reset timer 118 to begin timing a new time interval until the next signal to activate in-line monitoring apparatus 20 will be sent.

In an alternate embodiment of the invention, an optional time delay unit 120 may be activated once the presence of particulate matter is detected. This serves to allow a predetermined amount of time for the detected particulate matter to settle, thus avoiding inaccurate measurements due to turbidity of the liquid flowing through the in-line monitoring apparatus.

It will be appreciated by persons skilled in the art, that the present invention is not limited by what has been shown and discribed hereinabove merely by way of illustrative example. Rather, the scope of the present invention, is limited solely by the claims, which follow.

What is claimed is:

1. In-line monitoring apparatus, for monitoring particulate matter in a liquid stream, which includes:
   an inlet for permitting ingress of a liquid stream into said in-line monitoring apparatus;
   an outlet for discharging a liquid stream from said in-line monitoring apparatus;
   first and second liquid flow paths each arranged to conduct a liquid flow between said inlet and said outlet;
   an in-line particulate matter sampling unit arranged along said first flow path for permitting therein accumulation of particulate matter suspended in a liquid flow between said inlet and outlet, and having apparatus for measuring particulate matter accumulations therein;
   apparatus for separating particulate matter from a liquid stream entering said inlet, and for providing the particulate matter to said in-line sampling unit;
   first and second valves for selectably permitting liquid flow along said first and second flow paths, respectively, wherein said first valve is arranged downstream of said in-line sampling unit; and
   control apparatus for operating said in-line monitoring apparatus in either of a first and second operative modes, wherein in said first mode, said second valve is closed so as to prevent a through flow of liquid along said second flow path, and said first valve is open, and in said second mode, said second valve is open so as to permit a through flow of liquid along said second flow path, and said first valve is closed, and wherein, in said first mode, said in-line sampling unit is operative to permit entry and accumulation of particulate matter therein for measurement by said in-line monitoring apparatus, and in said second mode, a flow of liquid along said second flow path passes through said in-line sampling unit so as to remove the particulate matter accumulations therefrom so as to flush out any particulate matter as may have accumulated in said inline sampling unit, wherein said in-line sampling unit includes:

at least one sampling chamber for receiving an accumulation of particulate matter; and at least one apparatus for detecting the presence of at least a predetermined volume of particulate matter in said at least one sampling chamber, said at least one apparatus being operative to provide to said control apparatus an output signal indicative of said at least predetermined volume of particulate matter accumulation, and wherein said in-line monitoring apparatus also includes flow measuring apparatus for measuring the volumetric flow rate of a liquid flowing between said inlet and said outlet operative to provide and output signal to said control apparatus indicative of a rate of liquid flow, and wherein said control apparatus is further operative to evaluate the concentration of particulate matter suspended in the liquid stream per unit flow.

2. Apparatus according to claim 1, wherein said control apparatus is operable to activate said in-line monitoring apparatus in said first operative mode until detection of said at least a predetermined concentration of particulate matter, and wherein, in response to an output signal received from said apparatus for detecting, said control apparatus is operative to switch said in-line monitoring apparatus to said second operative mode for removal of particulate matter from said in-line sampling unit.

3. Apparatus according to claim 2, wherein, subsequent to said removal of particulate matter from said in-line sampling unit by said second operative mode, said control apparatus is operative to switch said in-line monitoring apparatus from said second mode to said first mode.

4. Apparatus according to claim 2, wherein, subsequent to said removal of particulate matter from said in-line sampling unit, said control apparatus is selectably operable to operate said in-line monitoring apparatus in a third mode, during which said apparatus for detecting is inactive for a preselected period of time, after which said control apparatus reactivates said apparatus for detecting so as to operate said in-line monitoring apparatus in said first operative mode.

5. Apparatus according to claim 1, wherein the concentration of particulate matter that said in-line monitoring apparatus is operative to detect is at least approximately 100 ppm.

6. Apparatus according to claim 5, wherein the concentration of particulate matter that said in-line monitoring apparatus is operative to detect is at least approximately 50 ppm.

7. Apparatus according to claim 6, wherein the concentration of particulate matter that said in-line monitoring apparatus is operative to detect is at least approximately 1 ppm.

8. Apparatus according to claim 1, wherein said above-mentioned valves are solenoid-type switching valves.

9. Apparatus according to claim 1, wherein said apparatus for separating particulate matter from a liquid stream is a cyclone type device.

10. Apparatus according to claim 1, wherein said at least one sampling chamber includes a first lower smaller sampling chamber and a second upper larger sampling chamber.

11. Apparatus according to claim 10, and including apparatus for inducing settlement of particulate matter from said upper sampling chamber to said lower sampling chamber wherein said upper sampling chamber is formed so as to permit passage of particulate matter to said lower sampling chamber.

12. Apparatus according to claim 11, wherein said apparatus for inducing settlement of particulate matter includes an inclined conduit leading from said upper sampling chamber to said lower sampling chamber.

13. Apparatus according to claim 12, wherein said upper sampling chamber includes a floor element that is sloped as a funnel, so as to facilitate settling of particulate matter towards an aperture at the top said inclined conduit.

14. Apparatus according to claim 13 and further including a generally upward conduit leading out from said lower sampling chamber, for allowing a flow of liquid that has entered said lower sampling chamber via said inclined conduit, to exit it.

15. Apparatus according to claim 1, wherein said in-line monitoring apparatus includes at least one particulate matter separator along said second flow path, downstream of said in-line sampling unit and upstream of said second valve, for permitting an outflow of particulate matter flushed through said second flow path during activation in said second operative mode, thereby substantially preventing outflow of particulate matter thereof through said second valve.

16. Apparatus according to claim 1, wherein said in-line monitoring apparatus is arranged so as to tap in to a main-flow conduit such that a stream of liquid entering said in-line monitoring apparatus from the main flow conduit is a substantially representative sample of the liquid flowing through the main flow conduit containing a correspondingly representative volume of suspended particulate matter.

\* \* \* \* \*